US012214139B2

(12) United States Patent
Oren et al.

(10) Patent No.: US 12,214,139 B2
(45) Date of Patent: Feb. 4, 2025

(54) PULSATING POSITIVE AIRWAY PRESSURE DEVICES AND METHODS OF USE

(71) Applicant: University of Cincinnati, Cincinnati, OH (US)

(72) Inventors: Liran Oren, Mason, OH (US); Ephraim Gutmark, Cincinnati, OH (US); Mehmet Tomac, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 897 days.

(21) Appl. No.: 17/287,575

(22) PCT Filed: Nov. 1, 2019

(86) PCT No.: PCT/US2019/059301
§ 371 (c)(1),
(2) Date: Apr. 22, 2021

(87) PCT Pub. No.: WO2020/092857
PCT Pub. Date: May 7, 2020

(65) Prior Publication Data
US 2021/0393904 A1 Dec. 23, 2021

Related U.S. Application Data

(60) Provisional application No. 62/755,850, filed on Nov. 15, 2018, provisional application No. 62/754,936, filed on Nov. 2, 2018.

(51) Int. Cl.
*A61M 16/20* (2006.01)
*A61M 16/00* (2006.01)

(52) U.S. Cl.
CPC ...... *A61M 16/202* (2014.02); *A61M 16/0057* (2013.01); *A61M 16/024* (2017.08);
(Continued)

(58) Field of Classification Search
CPC .............. A61M 16/00; A61M 16/0003; A61M 16/0009; A61M 16/0057; A61M 16/0096;
(Continued)

(56) References Cited

U.S. PATENT DOCUMENTS

| 5,483,953 A | 1/1996 | Cooper |
| 6,708,690 B1 * | 3/2004 | Hete ................. A61M 16/0096 128/205.24 |

(Continued)

FOREIGN PATENT DOCUMENTS

| CN | 1341186 A | 3/2002 |
| CN | 101588833 A | 11/2009 |

(Continued)

OTHER PUBLICATIONS

JP Notification of Reasons for Rejection dated Jul. 31, 2023 pertaining to JP application No. 2021-523878 filed Apr. 30, 2021, pp. 1-5.

(Continued)

*Primary Examiner* — Colin W Stuart
(74) *Attorney, Agent, or Firm* — Dinsmore & Shohl LLP (57) ABSTRACT

Methods and systems for delivery of pulsated air to a user using a device including a flow generator to generate a continuous air flow, a first actuator comprising a pulsated flow delivery mechanism configured to generate a pulsated air flow from the continuous air flow based on a pre-determined duty cycle to vary a frequency of the pulsated air flow, a user interface configured to generate and deliver vortices of pulsated air to the user at the frequency of the pulsated air flow, and a set of tubing to couple the flow generator, the first actuator, and the user interface.

17 Claims, 7 Drawing Sheets

(52) U.S. Cl.
CPC ..... *A61M 2206/16* (2013.01); *A61M 2206/20* (2013.01); *A61M 2230/40* (2013.01)

(58) Field of Classification Search
CPC .............. A61M 16/021; A61M 16/022; A61M 16/024; A61M 16/06; A61M 16/0666; A61M 16/0672; A61M 16/10; A61M 16/20; A61M 16/201; A61M 16/202; A61M 2205/07; A61M 2205/33; A61M 2205/3331; A61M 2205/50; A61M 2206/00; A61M 2206/10; A61M 2206/16; A61M 2206/20; A61M 2206/22; A61M 2230/40

See application file for complete search history.

(56) References Cited

U.S. PATENT DOCUMENTS

| | | | |
|---|---|---|---|
| 6,754,912 | B1 | 6/2004 | Hayashi et al. |
| 6,763,832 | B1* | 7/2004 | Kirsch .............. A61M 16/0672 128/206.25 |
| 2009/0133695 | A1 | 5/2009 | Rao et al. |
| 2010/0147302 | A1 | 6/2010 | Selvarajan et al. |
| 2011/0048414 | A1* | 3/2011 | Hoekman ............. A61M 31/00 128/200.23 |
| 2013/0133654 | A1 | 5/2013 | Garde et al. |
| 2013/0263850 | A1* | 10/2013 | Acker ................ A61M 16/202 128/203.14 |
| 2014/0158127 | A1* | 6/2014 | Boucher ................ A61M 11/00 128/203.22 |
| 2014/0366877 | A1 | 12/2014 | Selvarajan et al. |
| 2015/0047638 | A1 | 2/2015 | Robey |
| 2015/0075529 | A1 | 3/2015 | Romano |
| 2015/0300385 | A1 | 10/2015 | Akagi et al. |
| 2016/0045696 | A1 | 2/2016 | Siriwardena et al. |
| 2016/0106949 | A1* | 4/2016 | Kohlmann ........ A61M 16/0051 128/205.24 |
| 2016/0193437 | A1 | 7/2016 | Bao et al. |
| 2016/0346495 | A1* | 12/2016 | Payton ............. A61M 16/0683 |

FOREIGN PATENT DOCUMENTS

| | | |
|---|---|---|
| CN | 101873875 A | 10/2010 |
| CN | 102762250 A | 10/2012 |
| CN | 102802709 A | 11/2012 |
| JP | H02267316 A | 11/1990 |
| JP | 2001090150 A | 4/2001 |
| JP | 2015517374 A | 6/2015 |
| JP | 2018519117 A | 7/2018 |
| WO | 2013019717 A1 | 2/2013 |
| WO | 2014017208 A1 | 1/2014 |
| WO | 2018022448 A1 | 2/2018 |

OTHER PUBLICATIONS

CN First Office Action dated Nov. 27, 2023 pertaining to CN application No. 201980079918.0 filed Jun. 3, 2021, pp. 1-13.
EP Extended European Search Report dated Jul. 4, 2022 pertaining to EP application No. 19879934.8 filed Apr. 27, 2021, pp. 1-13.
International Search Report mailed Jan. 16, 2020, in reference to co-pending PCT/US2019/059301 filed Nov. 1, 2019.
Written Opinion mailed Jan. 16, 2020, in reference to co-pending PCT/US2019/059301 filed Nov. 1, 2019.
CN Second Office Action dated May 13, 2024 pertaining to CN application No. 201980079918.0 filed Jun. 3, 2021, pp. 1-14.
CN Notification to Grant Patent Right dated Aug. 7, 2024 pertaining to CN application No. 201980079918.0 filed Jun. 3, 2021, pp. 1-2.

* cited by examiner

PULSATING POSITIVE AIRWAY PRESSURE DEVICES AND METHODS OF USE

CROSS REFERENCE TO RELATED APPLICATIONS

The present specification claims priority to U.S. Provisional Patent Application Ser. Nos. 62/754,936, filed Nov. 2, 2018, and 62/755,850, filed Nov. 5, 2018, each entitled "APPLICATION OF PULSATING AND VORTEX AIRFLOW TO CONTINUOUS POSITIVE AIRWAY PRESSURE (CPAP) THERAPY," the entirety of each of which is incorporated by reference herein.

STATEMENT REGARDING FEDERALLY SPONSORED RESEARCH OR DEVELOPMENT

This invention was made with government support under IUH54HL119810-04 awarded by the National Institutes of Health. The government has certain rights in the invention.

TECHNICAL FIELD

The present specification generally relates to an air flow therapy device to treat obstructive sleep apnea ("OSA"), and, more specifically, to an air flow delivery therapy device configured to generate a pulsated airflow based on a pre-determined duty cycle to deliver to a user to treat OSA.

BACKGROUND

Obstructive sleep apnea ("OSA") is a chronic sleep-related breathing disorder that involves a decrease or complete halt in airflow despite efforts to breathe. OSA occurs when muscles relax during sleep and cause soft tissues surrounding a pharynx to collapse and obstruct an upper airway of a person. Continuous positive airway pressure (CPAP) therapy to treat OSA may include CPAP devices with a sealed mask interface to deliver a continuous airflow to users. However, such CPAP devices rely on the seal of the mask interface to generate sufficient pressure to deliver pressurized air to an upper airway of the user. The mask interface may be troublesome to the user when sleeping and/or inefficient due to dissipating pressure should the seal be disrupted.

Accordingly, a need exists for alternative devices for delivery of airflow to a user, such as one suffering from OSA, and methods of use of such devices.

SUMMARY

According to the subject matter of the present disclosure, and in one embodiment, a device for delivery of pulsated air to a user may include a flow generator to generate a continuous air flow, at least one actuator comprising a pulsated flow delivery mechanism configured to generate a pulsated air flow from the continuous air flow based on a pre-determined duty cycle to vary a frequency of the pulsated air flow, a user interface configured to generate and deliver vortices of pulsated air to the user at the frequency of the pulsated air flow, and a set of tubing to couple the flow generator, the at least one actuator, and the user interface.

In one other embodiment, a system for delivery of pulsated air to a user may include a device, a processor communicatively coupled to the device, and a non-transitory computer-readable memory storing instructions. The device may include a flow generator at an upstream position, at least one actuator comprising a pulsated flow delivery mechanism, a user interface at a downstream position, and a set of tubing. The instructions may, when executed by the processor, cause the processor to: generate a continuous air flow via the flow generator for receipt at the at least one actuator, generate via the pulsated flow delivery mechanism a pulsated air flow from the continuous air flow based on a pre-determined duty cycle to vary a frequency of the pulsated air flow, and generate and deliver vortices of pulsated air to the user at the frequency of the pulsated air flow through a distal portion of the set of tubing coupled to the user interface at the downstream position disposed downstream of the pulsated flow delivery mechanism.

In yet another embodiment, a method for delivery of pulsated air to a user may include generating vortices of pulsated air at a variable frequency based on a pre-determined duty cycle utilizing a device. The device may include a flow generator at an upstream position, at least one actuator comprising a pulsated flow delivery mechanism configured to generate a pulsated air flow at the variable frequency based on the pre-determined duty cycle, a user interface at a downstream position, and a set of tubing to couple the flow generator, the at least one actuator, and the user interface. The method may further include monitoring breathing pressure of the user via one or more pressure sensors communicatively coupled to the device, and delivering the vortices of pulsating air to the user in coordination with a negative breathing pressure of the user as sensed by the one or more pressure sensors.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Referring generally to the figures, embodiments of the present disclosure are directed to an air flow delivery therapy device configured to generated a pulsated air flow as vortices of air flow to deliver to a user based on a pre-determined duty cycle. The pulsated air flow is generated based on the pre-determined duty cycle to effect a variable pulsation, and vortices are generated when the pulsated air flow is released to atmosphere at the variable pulsation, as described in greater detail below. Reference will now be made in detail to embodiments of such air flow (e.g., jet) delivery therapy devices, examples of which along with components and systems are illustrated in the accompanying drawings. Wherever possible, the same reference numerals will be used throughout the drawings to refer to the same or like parts. Various embodiments of the tools will be described in further detail herein with specific reference to the appended drawings.

Patient compliance with Continuous Positive Airway Pressure (CPAP) therapy in treating obstructive sleep apnea (OSA) remains a major cause of treatment failure. OSA is a chronic sleep-related breathing disorder that involves a decrease or complete halt in airflow despite an ongoing effort to breathe. OSA occurs when muscles relax during sleep and cause soft tissues in a posterior pharynx of a person to collapse and obstruct an upper airway of the person. OSA is most likely to occur during an inspiration phase of respiration during sleep, which inspiration phase is associated with generation of negative intrathoracic pressure. Because the pressure in the lungs is less than the (atmospheric) pressure outside the nares of a person, air entrains into the upper airway as an air flow generated by a passive mechanism of a pressure difference between the lungs and atmosphere. For a person with OSA, the collapse of the soft tissue of the upper airway to lead to airway obstruction is likely to occur because of such negative pressure existing within the upper airway during inspiration.

Such an airway obstruction may lead to reductions or complete pauses in breathing during sleep, and the brain may respond to the resulting hypoxia and hypercapnia by alerting the body to cause a brief arousal from sleep that restores normal breathing. Such a disruptive pattern may occur hundreds of times each night due to OSA. Further, OSA may be independently associated with a wide variety of side effects including daytime sleepiness and fatigue, drowsy driving with increased risk of motor vehicle accidents, cardiovascular morbidities (e.g., hypertension, stroke), metabolic syndrome and type 2 diabetes, nonalcoholic fatty liver disease, perioperative complications, and premature death.

CPAP therapy to treat OSA operates to splint or provide the upper airway with positive pressure to prevent collapse of the soft tissues and thus prevent airway obstruction. With CPAP therapy, air flow may be actively pushed into the upper airway of a person due to the provided positive (airway) pressure for which the pressure from the air flow applied to a lumen of the upper airway is greater than the pressure applied to the upper airway from the surrounding soft tissue. The pneumatic splint created and applied through the provided positive pressure generated by such CPAP therapy maintains an open upper airway to prevent collapse of the soft tissues and thus prevent airway obstruction.

However, generally due to a discomfort related to a seal mask interface of such CPAP devices to maintain a sufficient positive pressure about at least one breathing passage of a user to prevent airway obstruction, patient noncompliance undermines the effect of such CPAP devices in CPAP therapy. Further, to deliver positive pressurized air to the upper airway of a patient with such CPAP devices including a seal mask interface to deliver continuous air flow characterized by a continuous motion of air particles along specific path lines, such CPAP devices must maintain a tight seal between the seal mask interface and the at least one breathing passage on a face of the user.

In embodiments, the pulsated air flow delivery therapy device described herein is configured to reduce or eliminate such a need for the tightly sealed interface between the device and the face of the user. The pulsated air flow delivery therapy device thus may improve patient compliance with use of less intrusive and covering devices throughout a patient sleep cycle. The pulsated air flow delivery therapy device is configured to generate a vortex airflow, which does not require a tight interface between a user interface and at least one breath passage of a patient. Rather, properties of the generated vortex airflow enable a flow to pressurize the airway and effectively splint the upper airway with sufficient positive pressure to prevent collapse of soft tissues and thus prevent airway obstruction. The pulsated air flow delivery therapy device is configured to generate the vortex airflow as pulsating and consists of a train of vortices that include rotating regions along an axis line. The vortices formed with vortex airflow may be applied as toroid pulses that are ring-shaped and configured to travel further along the axis line without losing structure than the continuous air flow of a continuous motion of air particles along specific path lines. Such a further traveled distance without a loss of structure may provide a positive pressure sufficient to splint an upper airway to keep it open without requiring a tight seal between the user interface and at least one breathing passage of the user.

Figure 1:
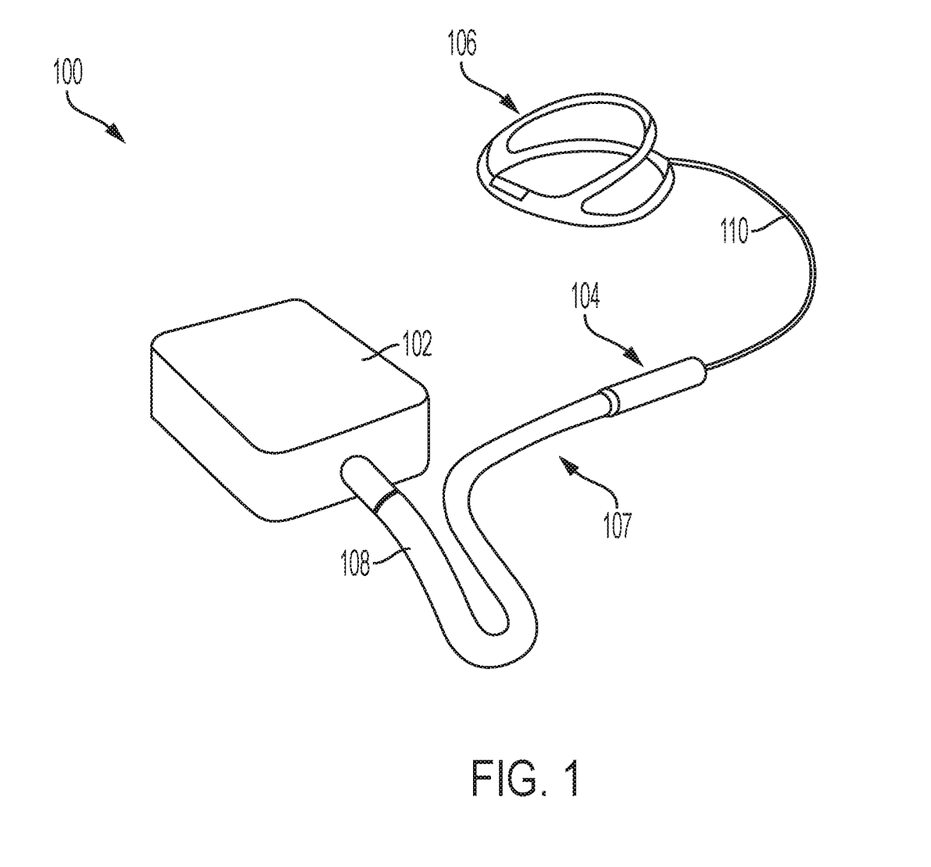
FIG. 1 is a device to deliver vortices of pulsated air to a user, according to one or more embodiments shown and described herein.
Figure 2:
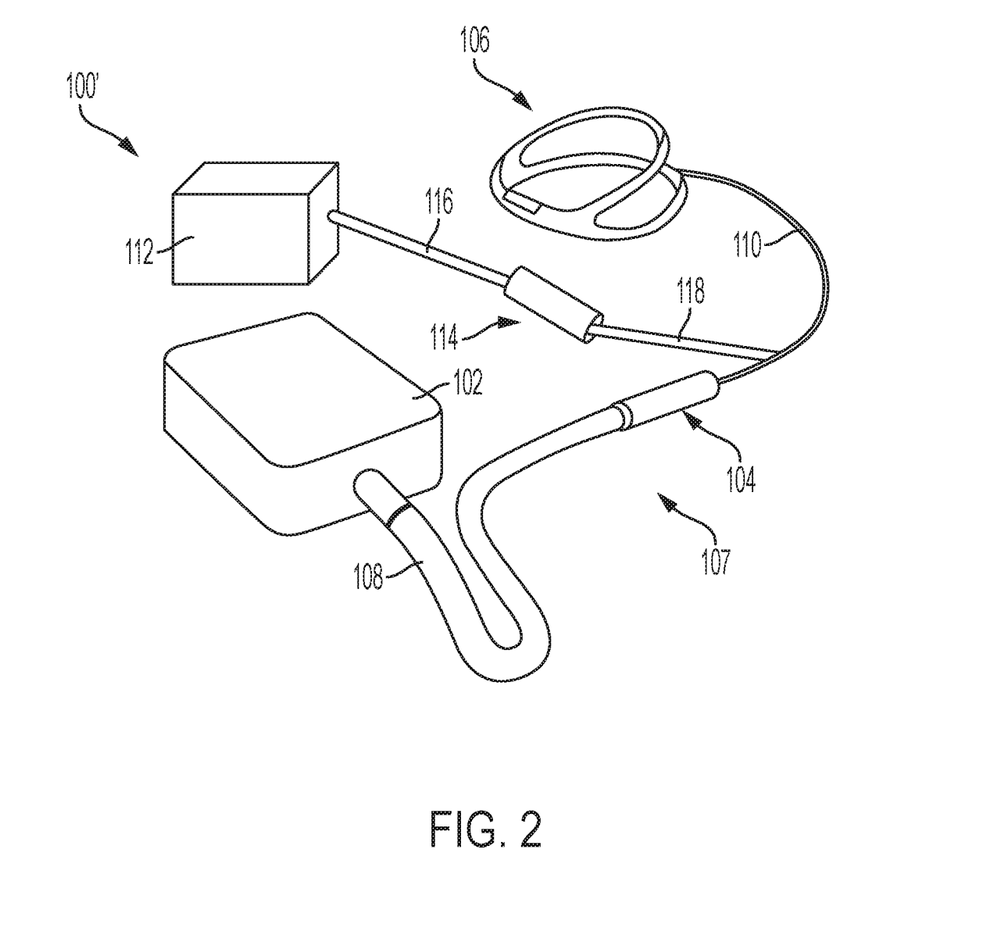
FIG. 2 is another embodiment of a device to deliver vortices of pulsated air to a user, according to one or more embodiments shown and described herein.

Referring to FIG. 1, a device 100 may include a flow generator 102, at least one actuator such as a first actuator 104, a user interface 106, and a set of tubing to couple the flow generator 102, the first actuator 104, and the user interface 106. Tubing 108 is disposed between to couple the flow generator 102 and the first actuator 104, and tubing 110 is disposed between to couple the first actuator 104 and the user interface 106. Referring to FIG. 2, a device 100' may include the components of the device 100 and further include a vacuum source 112 and a second actuator 114. The set of tubing 107 may further include tubing 116 disposed between to couple the vacuum source 112 and the second actuator 114 and tubing 118 disposed between to couple the second actuator 114 with tubing 110 in a downstream position of the first actuator 104, as will be described in greater detail below to enhance an applied pulsation.

In an embodiment, the devices 100, 100' of FIGS. 1-2 for delivery of pulsated air to a user are illustrated to include the flow generator 102 to generate a continuous air flow. The devices 100, 100' further include at least one actuator, such as the first actuator 104. The at least one actuator, such as the first actuator 104, may include a pulsated flow delivery mechanism 316, as described in greater detail below and illustrated in FIG. 5 The pulsated flow delivery mechanism 316 is configured to generate a pulsated air flow from the continuous air flow provided by the flow generator 102 based on a pre-determined duty cycle to vary a frequency of the pulsated air flow. Thus, the pulsated air flow that is generated is pulsating at a specific frequency at which each pulse is converted into a vortex (of multiple vortices 126) released to atmosphere at the specific frequency at a distal tubing portion at the user interface 106 as described in greater detail below. The distal tubing portion may include a distal portion of or coupled to the tubing 110 configured to release the pulsated air flow to atmosphere, such as the nare tubes 122, 124 of the user interface 106A of FIG. 3A or the curved nare tubes 132, 134 of the user interface 106B of FIG. 3B, which are described in greater detail below. The frequency of such pulsation and consequently the release of vortices 126 may vary based on the pre-determined duty cycle.

Referring to the device 100' of FIG. 2, in another embodiment, the at least one actuator may further include a second actuator 114 communicatively coupled to a vacuum source 112 and disposed downstream of the first actuator 104 toward a user interface 106. The second actuator 114 may be configured to open when the first actuator 104 is in the off position to generate negative pressure, and to close when the first actuator 104 is in the on position to enhance a strength of the pulsated air flow generated by the first actuator 104. For example, the first actuator 104 and the second actuator 114 may be valves, and the second actuator 114 may be downstream of the first actuator 104 and connected to the vacuum source 112. The second actuator 114 may be configured to be open when the first actuator 104 that creates the pulsated air flow is closed, and the second actuator 114 may be configured to close before the first actuator 104 is opened such as if the first actuator 104 and the second actuator 114 are out-of-phase from one another. Such an implementation is configured to generate negative pressure (e.g., pressure that is less than atmospheric) within the tubing 110 located past the first actuator 104 through the tubing 118 disposed downstream of the second actuator 114. The generated negative pressure acts as a suction force to enhance momentum of the pulsated air flow that is released when the first actuator 104 opens.

The devices 100, 100' further include a user interface 106 configured to generate and deliver vortices 126 (FIG. 3A) of pulsated air to the user at the frequency of the pulsated air flow and include a set of tubing 107 (such as tubing 108, 110 of FIG. 1 or tubing 108, 110, 116, 118 of FIG. 2) to couple the flow generator 102, the at least actuator 104, and the user interface 106. As a non-limiting example, for a flow rate condition, a stronger pulsated air flow is generated when an open period in the pre-determined duty cycle is shortened and/or when the vacuum source 112 of FIG. 2 is utilizing with the second actuator 114 as described herein. An increase in pulse strength may occur due to the shortening of the duty cycle of the first actuator 104 allowing for a pressure buildup behind (e.g., upstream) the first actuator 104 when closed, which pressure buildup may act as the driving force of energy that is converted into a higher velocity of increased momentum in each generated pulse when the first actuator 104 is opened. The magnitude of the resulting driving pressure may further be enhanced by inducing negative pressure in the tubing 110 in front (e.g., downstream) of the first actuator 104 as an overall pressure drop across the first actuator 104 is then increased. Each pulsated air flow from the first actuator 104 may be converted into a vortex at an exit of the tubing 110 downstream of the first actuator 104. Stronger pulses and corresponding stronger vortices 126 may thus be generated when an open period of the pre-determined duty cycle is shortened, such as a 20/80 duty cycle compared to a 50/50 duty cycle, to result in an increase overall pressure drop across the first actuator 104 configured to generate such pulses of pulsated air flow.

In embodiments, a proximal portion of the set of tubing 107 is communicatively coupled to the flow generator 102 at an upstream position. The user interface 106 is disposed at a downstream position and includes a distal portion of the set of tubing 107 (as shown at a distal end of the tubing 110 disposed between the at least one actuator and the user interface 106). The distal portion of the set of tubing 107 is configured to convert the pulsated air flow into the vortices 126 (FIG. 3A) of pulsated air upon release to atmosphere through the distal portion of the set of tubing 107. The vortices of pulsated air may be release as ring-shaped, or toroid, forms of air.

By way of example, and not as a limitation, the continuous air flow is received by the pulsated flow delivery mechanism 316 (e.g., of the first actuator 104) at a percentage associated with a first duty cycle value of the pre-determined duty cycle, and the continuous air flow is blocked from reception at a percentage associated with a second duty cycle value of the pre-determined duty cycle. The pre-determined duty cycle may include a 50/50 duty cycle, a 30/70 duty cycle, or a 20/80 duty cycle, such that the first duty cycle value is 50, 30, or 20, and the second duty cycle value is respectively 50, 70, or 80. It is within the scope of this disclosure that other duty cycles ranges may be used as the pre-determined duty cycle.

Referring back to FIG. 1, the pulsated flow delivery mechanism 316 (e.g., of the first actuator 104) may include one or more ports of a valve such as a solenoid valve configured to switch between open and closed positions based on the pre-determined duty cycle. In an embodiment, the at least one actuator includes the solenoid valve as the first actuator 104 and the pulsated flow delivery mechanism 316 is configured to switch the solenoid valve between (i) an on position during an on portion of the pre-determined duty cycle to receive the continuous air flow from the flow generator 102 and convert to the pulsating air flow and (ii) an off position during an off portion of the pre-determined duty cycle to block the continuous air flow from the flow generator 102. As a non-limiting example, the continuous air flow entering the first actuator 104 from the tube 108 coupled to the flow generator 102 is converted by the pulsated flow delivery mechanism 316 into the pulsated air flow by switching on and off ports in the solenoid valve to respectively enable or block an air flow path, and the frequency of the pulsated air flow may be varied based on the pre-determined duty cycle of the pulsated flow delivery mechanism 316. The duty cycle of the solenoid valve, for example, may vary based on manipulation of an "open/close" state. As a non-limiting example, to generate a pulsated air flow at 1 Hz, the solenoid valve having a 50/50 duty cycle may be open for 0.5 seconds and closed for 0.5 seconds, while the solenoid valve having a 30/70 duty cycle may be open for 0.3 seconds and closed for 0.7 seconds. In an embodiment, the vortices 126 may be generated and delivered at 20-30 Hz. For example, at 20 Hz, 20 vortices 126 may be generated and delivered per second to a user. Thus, over an 3-5 second inhale of the user, at 20 Hz, about 60 vortices 126 may be delivered to the user. An exhale of the user may be 5-7 seconds at which the vortices are not delivered in an embodiment, as described in greater detail below with respect to FIG. 7, in which the breathing cycle of the user is monitored via one or more pressure sensors 312 (FIG. 5) in secondary tubing to capture pressure at nares of the user to coordinate with delivery of the vortices 126.

Pulsating air flow as a pulsating jet of air may thus be created using the solenoid valve from the continuous air flow as a continuous jet of air generated by the flow generator 102. A flow upstream of the solenoid valve is generated continuously to create the continuous air flow using the flow generator 102, which may be a flow source such as a pump. The continuous air flow is delivered to the solenoid valve via tubing 108 and converted at the solenoid valve into a pulsated air flow. The pulsated air flow is delivered to the user interface 106 via tubing 110, a distal end of which releases vortices 126 at the user interface 106 generated from the pulsated air flow for receipt within, for example, nares of a user of the device 100, 100'.

Figure 3A:
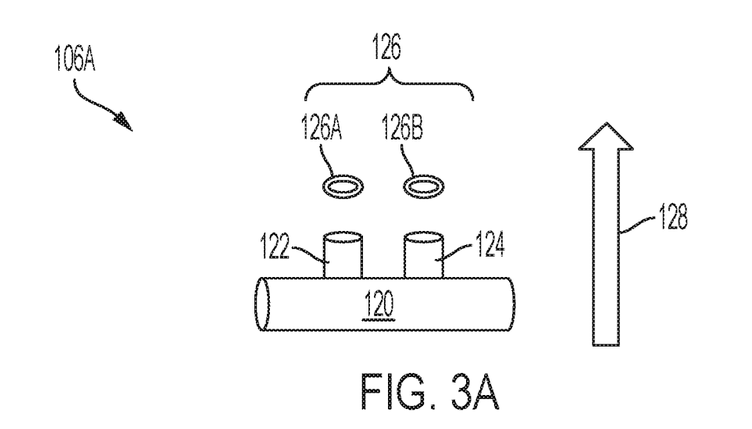
FIG. 3A is another embodiment of a user interface of the device of FIG. 1 or 2 to deliver vortices of pulsated air, according to one or more embodiments shown and described herein.
Figure 3B:
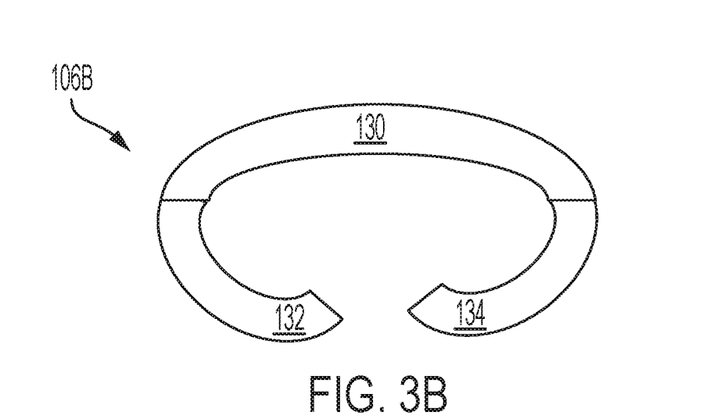
FIG. 3B is yet another embodiment of a user interface of the device of FIG. 1 or 2 to deliver vortices of pulsated air, according to one or more embodiments shown and described herein.

Referring to FIGS. 3A and 3B, non-liming examples of the user interface 106 include respective a user interface 106A and a user interface 106B. The user interface 106A of FIG. 3A is configured to deliver vortices 126A, 126B to a user's nostrils (e.g., nares) in a direction of arrow 128 via respective nare tubes 122, 124 extending from tube 120, which tube 120 is configured to be coupled with the tubing 110 of the set of tubing 107. In FIG. 3B, the user interface 106B includes a headset 130 to be coupled with the tubing 110 and a pair of curved nare tubes 132, 134 configured to deliver vortices 126 to the nares of a user. In embodiments, the head set may include a foam cap coupled to nasal buds comprising a plastic to deliver the vortices 126 to the nares of a user.

Referring back to FIG. 2, the at least one actuator may further include a second solenoid valve as the second actuator 114 communicatively coupled to the vacuum source 112 and disposed downstream of the solenoid valve as the first actuator 104 toward the user interface 106. The second solenoid valve is configured to close when the solenoid valve is in the on position and configured to open when the solenoid valve is in the off position to generate negative pressure.

Figure 4:
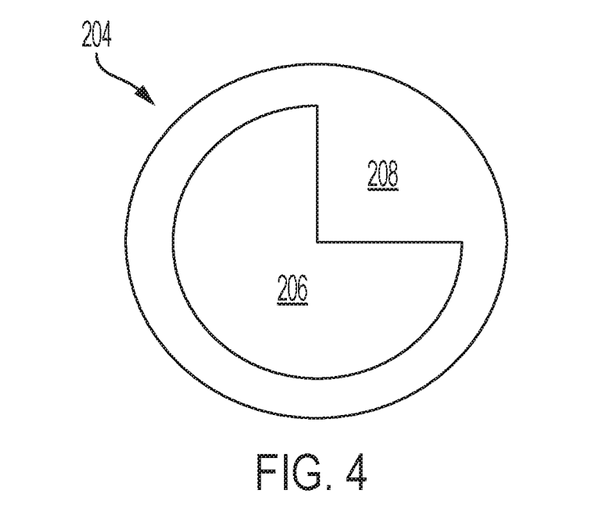
FIG. 4 is an embodiment of a rotary valve of the devices of FIG. 1 or 2 to generate pulsated air from a continuous air flow, according to one or more embodiments shown and describe herein.

In another embodiment, the pulsated flow delivery mechanism 316 (e.g., of the first actuator 104) may include a rotary valve 204 as shown in FIG. 4. The rotary valve 204 may be configured to include an aperture as an open port 206 and a solid surface as a closed port 208 such that the rotary valve is configured to switch between open and closed positions through valve rotation between the open port 206 and the closed port 208.

In an embodiment, the rotary valve 204 may be configured a fan wheel with at least one spinning wheels having edges defining one or more openings to correspond to open positions through which to generate pulses of pulsated air flow with reduced air attenuation. A thickness of the at least one spinning wheel may effect a reduced air attenuation to reduce noise flow through cutting tapered edges of increase aerodynamic property as compared to sharp blunt edges. The cutting tapered edges may include smooth corners and a tear shape to reduce noise attenuation. Additionally or alternatively, noise attenuation may be reduced with the rotary valve 204 or other configurations of the pulsated flow delivery mechanism 316 through use of one or more muffler components. In an embodiment, the muffler components comprises an acoustic foam, which may be expandable, to absorb sound. A first muffler component may be disposed downstream of the first actuator 104 to reduce noise generated from the pulsated air flow being generate and directed downstream of the first actuator 104 in the tubing 110. In embodiments, a muffler component may additionally or alternatively be disposed upstream of the first actuator 104 in tubing 108 to reduce noise of continuous air flow being directed to the first actuator 104 for conversion into pulsated air flow.

In alternative embodiments, the pulsated flow delivery mechanism 316 (e.g., of the first actuator 104) may include one of a pump, a float switch, a paddle wheel, a j et component, or a plunger. As a pump, the pulsated flow delivery mechanism 316 may be a peristaltic pump, a diaphragm pump, a piston pump, a centrifugal pump, an electromagnetic pump, an impedance pump, a Knudsen pump, a rotary vane pump, or a vacuum pump.

Figure 5:
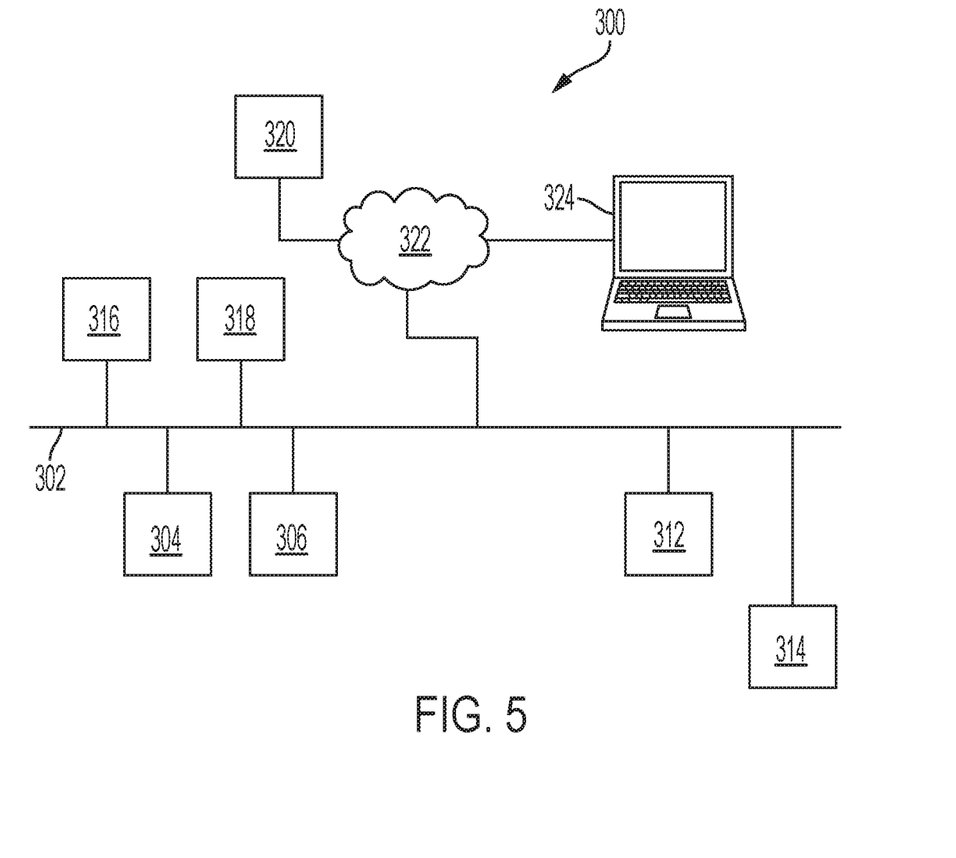
FIG. 5 schematically illustrates a system for implementing computer and software based methods to utilize the tools of FIGS. 1 and/or 2, according to one or more embodiments shown and described herein.

Referring to FIG. 5, a system 300 for implementing a computer and software-based method to utilize the pulsated air delivery devices, as shown in FIGS. 1 and 2, may be implemented along with using a graphical user interface (GUI) displaying, for example, monitored flow rates and/or monitored breathing pressure of a user of the pulsated air delivery devices. The GUI may be accessible on a display at a user workstation (e.g., a computing device 324), for example. The system 300 includes a communication path 302, one or more processors 304, a memory component 306, one or more pressure sensors 312 to monitor breathing pressure of a user, for example, a storage or database 314, a pulsated flow delivery mechanism 316, a network interface hardware 318, a network 322, a server 320, and at least one computing device 326. The various components of the system 300 and the interaction thereof will be described in detail below.

In some embodiments, the system 300 is implemented using a wide area network (WAN) or network 322, such as an intranet or the Internet. The computing device 324 may include digital systems and other devices permitting connection to and navigation of the network. Other system 300 variations allowing for communication between various geographically diverse components are possible. The lines depicted in FIG. 5 indicate communication rather than physical connections between the various components.

As noted above, the system 300 includes the communication path 302. The communication path 302 may be formed from any medium that is capable of transmitting a signal such as, for example, conductive wires, conductive traces, optical waveguides, or the like, or from a combination of mediums capable of transmitting signals. The communication path 302 communicatively couples the various components of the system 300. As used herein, the term "communicatively coupled" means that coupled components are capable of exchanging data signals with one another such as, for example, electrical signals via conductive medium, electromagnetic signals via air, optical signals via optical waveguides, and the like.

As noted above, the system 300 includes the processor 304. The processor 304 can be any device capable of executing machine readable instructions. Accordingly, the processor 304 may be a controller, an integrated circuit, a microchip, a computer, or any other computing device. The processor 304 is communicatively coupled to the other components of the system 300 by the communication path 302. Accordingly, the communication path 302 may communicatively couple any number of processors with one another, and allow the modules coupled to the communication path 302 to operate in a distributed computing environment. Specifically, each of the modules can operate as a node that may send and/or receive data.

As noted above, the system 300 includes the memory component 306 which is coupled to the communication path 302 and communicatively coupled to the processor 304. The memory component 306 may be a non-transitory computer readable medium or non-transitory computer readable memory and may be configured as a nonvolatile or volatile computer readable medium. The memory component 306 may comprise RAM, ROM, flash memories, hard drives, or any device capable of storing machine readable instructions such that the machine readable instructions can be accessed and executed by the processor 304. The machine readable instructions may comprise logic or algorithm(s) written in any programming language such as, for example, machine language that may be directly executed by the processor, or assembly language, object-oriented programming (OOP), scripting languages, microcode, etc., that may be compiled or assembled into machine readable instructions and stored on the memory component 306. Alternatively, the machine readable instructions may be written in a hardware description language (HDL), such as logic implemented via either a field-programmable gate array (FPGA) configuration or an application-specific integrated circuit (ASIC), or their equivalents. Accordingly, the methods described herein may be implemented in any conventional computer programming language, as pre-programmed hardware elements, or as a combination of hardware and software components. In embodiments, the system 300 may include the processor 304 communicatively coupled to the memory component 306 that stores instructions that, when executed by the processor 304, cause the processor to perform one or more functions as described herein.

Still referring to FIG. 5, as noted above, the system 300 comprises the display such as a GUI on a screen of the computing device 324 for providing visual output such as, for example, information, monitored flow status as described above, graphical reports, messages, alerts, or a combination thereof. The display on the screen of the computing device 324 is coupled to the communication path 302 and communicatively coupled to the processor 304. Accordingly, the communication path 302 communicatively couples the display to other modules of the system 300. The display can include any medium capable of transmitting an optical output such as, for example, a cathode ray tube, light emitting diodes, a liquid crystal display, a plasma display, or the like. Additionally, it is noted that the display or the smart device 324 can include at least one of the processor 304 and the memory component 306. While the system 300 is illustrated as a single, integrated system in FIG. 5, in other embodiments, the systems can be independent systems.

The system 300 comprises the one or more pressure sensors 312 to monitor breathing pressure of a user, and a pulsated flow delivery mechanism 316 to generate the pulsated vortices of air to deliver to the user as described herein. The one or more pressure sensors 312 and the pulsated flow delivery mechanism 316 are coupled to the communication path 302 and communicatively coupled to the processor 304. As will be described in further detail below, the processor 304 may process the input signals received from the system modules and/or extract information from such signals.

The system 300 includes the network interface hardware 318 for communicatively coupling the system 300 with a computer network such as network 322. The network interface hardware 318 is coupled to the communication path 302 such that the communication path 302 communicatively couples the network interface hardware 318 to other modules of the system 300. The network interface hardware 318 can be any device capable of transmitting and/or receiving data via a wireless network. Accordingly, the network interface hardware 318 can include a communication transceiver for sending and/or receiving data according to any wireless communication standard. For example, the network interface hardware 318 can include a chipset (e.g., antenna, processors, machine readable instructions, etc.) to communicate over wired and/or wireless computer networks such as, for example, wireless fidelity (Wi-Fi), WiMax, Bluetooth, IrDA, Wireless USB, Z-Wave, ZigBee, or the like.

Still referring to FIG. 5, data from various applications running on the computing device 324 can be provided from the computing device 324 to the system 300 via the network interface hardware 318. The computing device 324 can be any device having hardware (e.g., chipsets, processors, memory, etc.) for communicatively coupling with the network interface hardware 318 and a network 322. Specifically, the computing device 324 can include an input device having an antenna for communicating over one or more of the wireless computer networks described above.

The network 322 can include any wired and/or wireless network such as, for example, wide area networks, metropolitan area networks, the Internet, an Intranet, satellite networks, or the like. Accordingly, the network 322 can be utilized as a wireless access point by the computing device 324 to access one or more servers (e.g., a server 320). The server 320 and any additional servers generally include processors, memory, and chipset for delivering resources via the network 322. Resources can include providing, for example, processing, storage, software, and information from the server 320 to the system 300 via the network 322. Additionally, it is noted that the server 320 and any additional servers can share resources with one another over the network 322 such as, for example, via the wired portion of the network, the wireless portion of the network, or combinations thereof.

Figure 6:
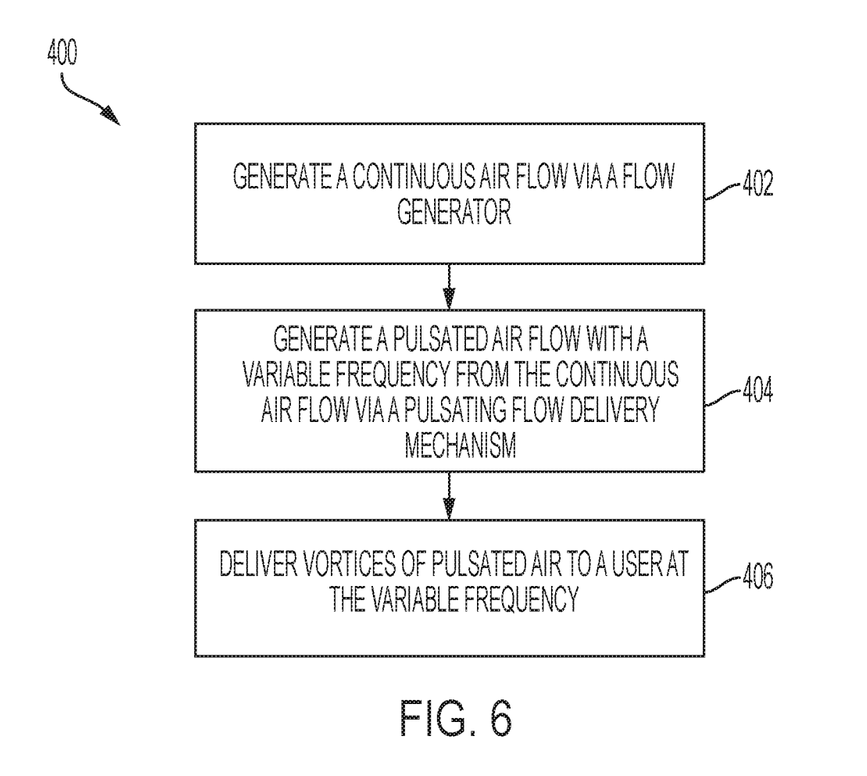
FIG. 6 is a flow chart of a process for delivery of pulsated air utilizing the devices and/or components of FIGS. 1-4 and the system of FIG. 5, according to one or more embodiments shown and described herein.
Figure 7:
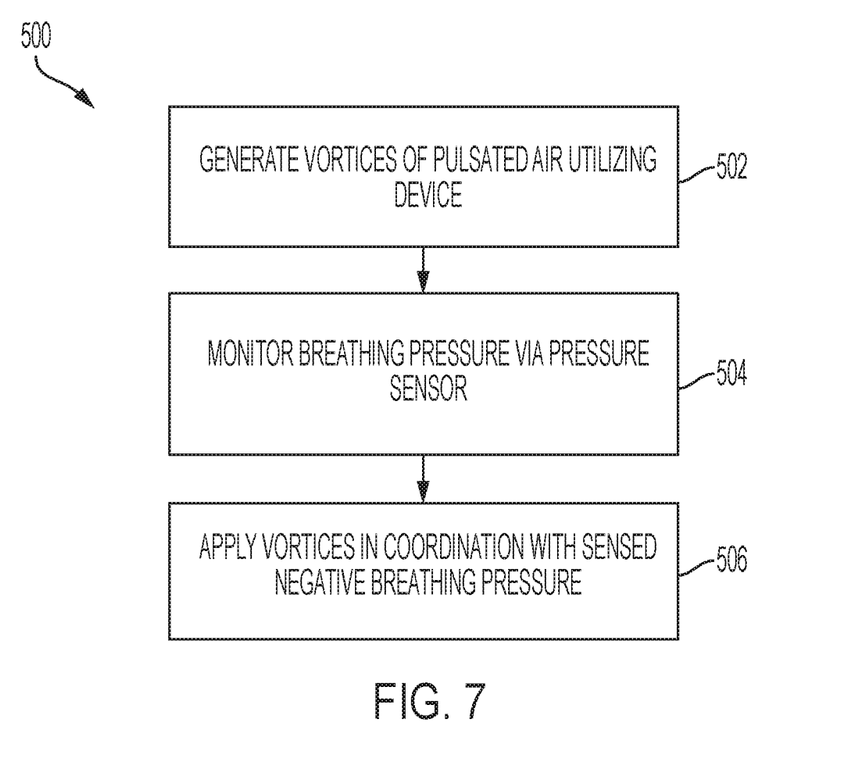
FIG. 7 is a flow chart of another process for delivery of pulsated air utilizing the devices and/or components of FIGS. 1-4 and the system of FIG. 5, according to one or more embodiments shown and described herein.

In embodiments, the system 300 for delivery of pulsated air to a user as described herein may include the device 100, 100', which include the flow generator 102 at an upstream position, at least one actuator (e.g., the first actuator 104) comprising the pulsated flow delivery mechanism 316, the user interface 106 at a downstream position, and the set of tubing 107. The system 300 may further include a processor 304 communicatively coupled to the device 100, 100' and a non-transitory computer-readable memory 306 communicatively coupled to the processor 304. The memory 306 may store instructions that, when executed by the processor 304, cause the processor 304 to follow one or more functions, such those set forth in blocks 402-406 or 502-506 of the processes 400, 500 respectively described in greater detail below. In an embodiment, the instructions may be to generate a continuous air flow via the flow generator 102 for receipt at the at least one actuator, such as the first actuator 104. The instructions may further be to generate, via the pulsated flow delivery mechanism 316, a pulsated air flow from the continuous air flow provided by the flow generator 102. The generated pulsated air flow is based on a predetermined duty cycle to vary a frequency of the pulsated air flow. The instructions may further be to generate and deliver vortices of pulsated air to the user at the frequency of the pulsated air flow through a distal portion of the set of tubing 107 coupled to the user interface 106 at the downstream position disposed downstream of the pulsated flow delivery mechanism 316. In embodiments, the instructions may further be to monitor breathing pressure of the user via one or more pressure sensors 312 communicatively coupled to the device 100, 100', and to apply the vortices 126 of pulsating air to the user in coordination with negative breathing pressure of the user as sensed by the one or more pressure sensors 312.

FIG. 6 is a flow chart of a process 400 for delivery of pulsated air to a user, such as a process implemented by the system 300 as described above. In block 402, a continuous air flow may be generated via the flow generator 102 for receipt at the at least one actuator (e.g., the first actuator 104). In block 404, the pulsated air flow from the continuous air flow provided by the flow generator 102 may be generated at the variable frequency based on the pre-determined duty cycle via the pulsated flow delivery mechanism 316. In block 406, and vortices 126 of pulsated air may be generated and delivered to the user at the frequency of the pulsated air flow through a distal portion of the set of tubing 107 coupled to the user interface 106 at the downstream position disposed downstream of the pulsated flow delivery mechanism 316.

FIG. 7 is a flow chart of another process 500 for delivery of pulsated air to a user, such as a process implemented by the system 300 as described above. In block 502, vortices 126 of pulsated air are generated at a variable frequency based on a pre-determined duty cycle utilizing the device 100, 100'. The device 100, 100' includes the flow generator 102 at an upstream position, at least one actuator (e.g., the first actuator 104) comprising a pulsated flow delivery mechanism 316 configured to generate a pulsated air flow at the variable frequency based on the pre-determined duty cycle, the user interface 106 at a downstream position, and a set of tubing 107 to couple the flow generator 102, the at least actuator, and the user interface 106.

To generate vortices 126 of pulsated air at a variable frequency based on a pre-determined duty cycle in block 502, a continuous air flow may be generated via the flow generator 102 for receipt at the at least one actuator (e.g., the first actuator 104), the pulsated air flow from the continuous air flow provided by the flow generator 102 may be generated at the variable frequency based on the pre-determined duty cycle via the pulsated flow delivery mechanism 316, and vortices 126 of pulsated air may be generated and delivered to the user at the frequency of the pulsated air flow through a distal portion of the set of tubing 107 coupled to the user interface 106 at the downstream position disposed downstream of the pulsated flow delivery mechanism 316.

In block 504, breathing pressure of the user is monitored via the one or more pressure sensors 312 communicatively coupled to the device 100, 100'. The one or more pressure sensors 312 may be configured to monitor an intake of breath as a negative breathing pressure of the user and an exhale of breath as a positive breathing pressure of the user to monitor a user's breathing cycle and pattern. In block 506, the vortices 126 of pulsating air are delivered to the user in coordination with a negative breathing pressure of the user as sensed by the one or more pressure sensors 312. Such positive pressure delivery of the vortices 126 coordinated with the negative breathing pressure of the user may be able to further enhance momentum of the application of the vortices 126 to retain structure and provide the splint leading to an unobstructed airway.

The pulsated air flow delivery therapy devices described herein thus allow for an application of a vortex air flow for OSA therapy that may reduce or eliminate a need for a tightly sealed user mask interface as otherwise available for continuous air flow delivery therapy devices. A compromised mask seal of a mask interface for such continuous air flow delivery therapy devices may result in insufficient positive pressure to delivery to an upper airway as a majority of the continuous air flow may leak out from the mask interface instead of entering the upper airway and thus may reduce an effective positive pressure to splint the airway.

However, when vortex airflow pulsated air flow delivery therapy devices described herein is directed toward the nostrils (e.g., nares of a person as at least one breath passage), no such seal may be required as a majority of the vortices of pulsated air flow will enter into the upper airway due to celerity and penetration properties of the vortices to, upon entry, apply a required and sufficient positive pressure on the lumen of the upper airway to splint the airway and prevent airway obstruction.

It is noted that recitations herein of a component of the present disclosure being "configured" or "programmed" in a particular way, to embody a particular property, or to function in a particular manner, are structural recitations, as opposed to recitations of intended use. More specifically, the references herein to the manner in which a component is "configured" or "programmed" denotes an existing physical condition of the component and, as such, is to be taken as a definite recitation of the structural characteristics of the component.

It is noted that the terms "substantially" and "about" and "approximately" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

The invention claimed is:

1. A device for delivery of pulsated air to a user, the device comprising:
   a flow generator to generate a continuous air flow;
   at least one actuator comprising a pulsated flow delivery mechanism having one or more valves and configured to generate a pulsated air flow from the continuous air flow based on a pre-determined duty cycle to vary a frequency of the pulsated air flow;
   a user interface configured to generate and deliver vortices of pulsated air to the user at the frequency of the pulsated air flow; and
   a set of tubing to couple the flow generator, the at least one actuator, and the user interface;
   wherein the continuous air flow is received by the pulsated flow delivery mechanism at a percentage associated with a first duty cycle value of the pre-determined duty cycle, and the continuous air flow is blocked from reception at a percentage associated with a second duty cycle value of the pre-determined duty cycle, and wherein a decrease in the first duty cycle value relative to a base first duty cycle value causes the strength of the vortices generated to increase relative to the strength of the vortices generated with the base first duty cycle value, and an increase in the first duty cycle value relative to the base first duty cycle value causes the strength of the vortices to decrease relative to the strength of the vortices generated with the base first duty cycle value.

2. The device of claim 1, wherein the user interface is disposed at a downstream position and comprises a distal portion of the set of tubing, and the distal portion of the set of tubing is configured to convert the pulsated air flow into the vortices of pulsated air upon release to atmosphere.

3. The device of claim 2, wherein the vortices of pulsated air comprise ring-shaped forms of air.

4. The device of claim 1, wherein a proximal portion of the set of tubing is communicatively coupled to the flow generator at an upstream position.

5. The device of claim 1, wherein the pre-determined duty cycle comprises a 50/50 duty cycle, a 30/70 duty cycle, or a 20/80 duty cycle, such that the first duty cycle value is 50, 30, or 20, and the second duty cycle value is respectively 50, 70, or 80.

6. The device of claim 1, wherein the pulsated flow delivery mechanism comprises one or more ports of a solenoid valve configured to switch between open and closed positions.

7. The device of claim 1, wherein the pulsated flow delivery mechanism comprises a rotary valve configured to include an aperture as an open port and a solid surface as a closed port such that the rotary valve is configured to switch between open and closed positions through valve rotation between the open port and the closed port.

8. The device of claim 1, wherein the at least one actuator comprises a solenoid valve and the pulsated flow delivery mechanism is configured to switch the solenoid valve between (i) an on position during an on portion of the pre-determined duty cycle to receive the continuous air flow and convert to the pulsated air flow and (ii) an off position during an off portion of the pre-determined duty cycle to block the continuous air flow.

9. The device of claim 8, wherein the at least one actuator comprises a second solenoid valve communicatively coupled to a vacuum source and disposed downstream of the solenoid valve toward the user interface, the second solenoid valve configured to close when the solenoid valve is in the on position and configured to open when the solenoid valve is in the off position to generate negative pressure.

10. A system for delivery of pulsated air to a user, the system comprising:
a device comprising a flow generator at an upstream position, at least one actuator comprising a pulsated flow delivery mechanism having one or more valves, a user interface at a downstream position, and a set of tubing;
a processor communicatively coupled to the device; and
a non-transitory computer-readable memory storing instructions that, when executed by the processor, cause the processor to:
generate a continuous air flow via the flow generator for receipt at the at least one actuator;
generate via the pulsated flow delivery mechanism a pulsated air flow from the continuous air flow based on a pre-determined duty cycle to vary a frequency of the pulsated air flow; and
generate and deliver vortices of pulsated air to the user at the frequency of the pulsated air flow through a distal portion of the set of tubing coupled to the user interface at the downstream position disposed downstream of the pulsated flow delivery mechanism;
wherein the continuous air flow is received by the pulsated flow delivery mechanism at a percentage associated with a first duty cycle value of the pre-determined duty cycle, and the continuous air flow is blocked from reception at a percentage associated with a second duty cycle value of the pre-determined duty cycle, and wherein a decrease in the first duty cycle value relative to a base first duty cycle value causes the strength of the vortices generated to increase relative to the strength of the vortices generated with the base first duty cycle value, and an increase in the first duty cycle value relative to the base first duty cycle value causes the strength of the vortices to decrease relative to the strength of the vortices generated with the base first duty cycle value.

11. The system of claim 10, further comprising instructions to:
monitor breathing pressure of the user via one or more pressure sensors communicatively coupled to the device;
apply the vortices of pulsating air to the user in coordination with negative breathing pressure of the user as sensed by the one or more pressure sensors.

12. The system of claim 11, wherein the distal portion of the set of tubing is configured to convert the pulsated air flow into the vortices of pulsated air upon release to atmosphere.

13. The system of claim 12, wherein the vortices of pulsated air comprise ring-shaped forms of air.

14. A method for delivery of pulsated air to a user, the method comprising:
generating vortices of pulsated air at a variable frequency based on a pre-determined duty cycle utilizing a device comprising a flow generator at an upstream position, at least one actuator comprising a pulsated flow delivery mechanism having one or more valves and configured to generate a pulsated air flow from a continuous airflow generated by the flow generator at a percentage associated with a first duty cycle value of the pre-determined duty cycle and the continuous air flow is blocked from reception at a percentage associated with a second duty cycle value of the pre-determined duty cycle, wherein the pulsated air flow is generated at the variable frequency based on the pre-determined duty cycle, a user interface at a downstream position, and a set of tubing to couple the flow generator, the at least one actuator, and the user interface;
monitoring breathing pressure of the user via one or more pressure sensors communicatively coupled to the device; and
delivering the vortices of pulsating air to the user in coordination with a negative breathing pressure of the user as sensed by the one or more pressure sensors, wherein a decrease in the first duty cycle value relative to a base first duty cycle value causes the strength of the vortices generated to increase relative to the strength of the vortices generated with the base first duty cycle value, and an increase in the first duty cycle value relative to the base first duty cycle value causes the strength of the vortices to decrease relative to the strength of the vortices generated with the base first duty cycle value.

15. The method of claim 14, wherein generating vortices of pulsated air at the variable frequency based on the pre-determined duty cycle comprises:
generating a continuous air flow via the flow generator for receipt at the at least one actuator;
generating via the pulsated flow delivery mechanism the pulsated air flow from the continuous air flow at the variable frequency based on the pre-determined duty cycle; and
generating and delivering vortices of pulsated air to the user at the variable frequency of the pulsated air flow through a distal portion of the set of tubing coupled to the user interface at the downstream position disposed downstream of the pulsated flow delivery mechanism.

16. The system of claim 15, wherein the distal portion of the set of tubing is configured to convert the pulsated air flow into the vortices of pulsated air upon release to atmosphere.

17. The system of claim 16, wherein the vortices of pulsated air comprise ring-shaped forms of air.

* * * * *